(12) United States Patent
Lukacs

(10) Patent No.: US 7,329,420 B1
(45) Date of Patent: Feb. 12, 2008

(54) HERBAL REMEDY SYSTEM

(76) Inventor: Maria Lukacs, 4700 Cove Cir., #208, St. Petersburg, FL (US) 33708

( * ) Notice: Subject to any disclaimer, the term of this patent is extended or adjusted under 35 U.S.C. 154(b) by 0 days.

(21) Appl. No.: 11/398,907

(22) Filed: Apr. 6, 2006

(51) Int. Cl.
*A61K 36/00* (2006.01)
*A61K 36/13* (2006.01)
*A23L 1/08* (2006.01)

(52) U.S. Cl. .................. 424/742; 424/770; 424/725; 554/8; 426/48; 426/330.4

(58) Field of Classification Search .................. None
See application file for complete search history.

(56) References Cited

U.S. PATENT DOCUMENTS

| 5,510,000 | A | * | 4/1996 | Phan et al. .................. 162/111 |
| 5,947,275 | A | * | 9/1999 | Hess .......................... 206/210 |
| 6,780,825 | B2 | * | 8/2004 | Piterski et al. .............. 510/124 |
| 2006/0137702 | A1 | * | 6/2006 | Karerat et al. .............. 131/352 |

* cited by examiner

*Primary Examiner*—Susan Hoffman
*Assistant Examiner*—Catheryne Chen
(74) *Attorney, Agent, or Firm*—Edward P. Dutkiewicz

(57) ABSTRACT

A therapeutic mixture has essentially equal parts of eucalyptus globulus oil and pinus sylvestris oil and thymus vulgaris oil.

1 Claim, 2 Drawing Sheets

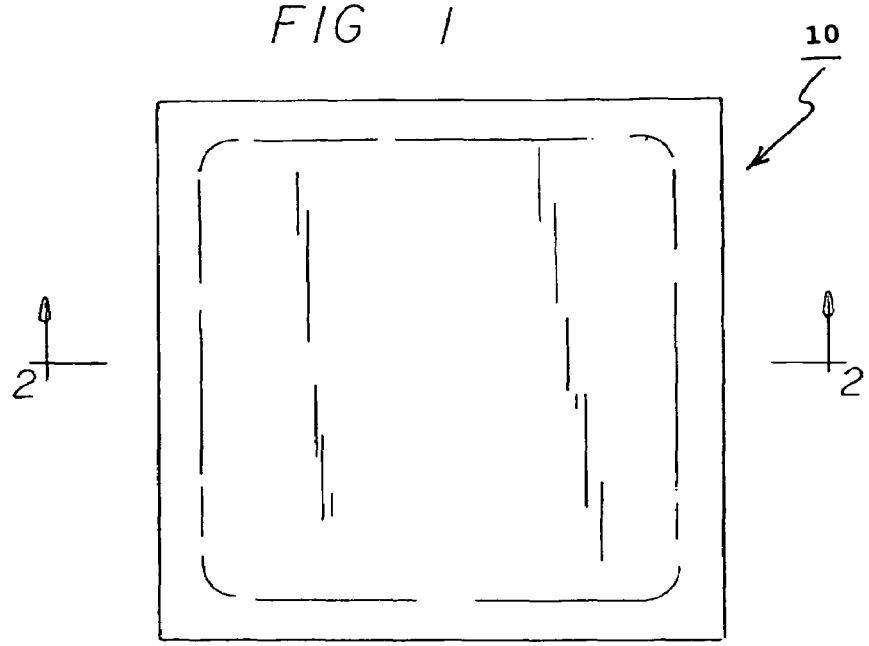
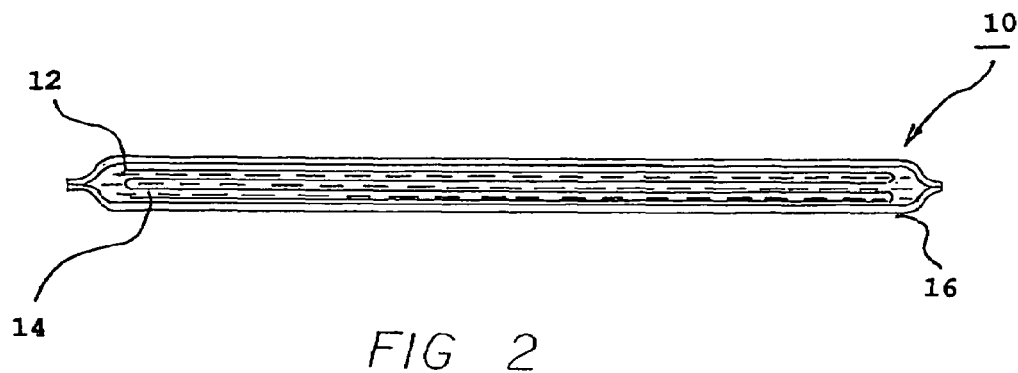

HERBAL REMEDY SYSTEM

BACKGROUND OF THE INVENTION

1. Field of the Invention

The present invention relates to an herbal remedy system and more particularly pertains to therapeutically treating patients suffering from a wide range of maladies.

2. Description of the Prior Art

The use of herbal remedies is known in the prior art. More specifically, herbal remedies of known compositions previously devised and utilized for the purpose of treating patients suffering from maladies are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,057,467 issued Oct. 9, 1962 to Williams relates to a Package for Treating Agents and Disposable Applicator Forming a Part Thereof. U.S. Pat. No. 4,740,398 issued Apr. 26, 1988 to Bouchette relates to a Binder Catalyst for an Antimicrobially Active, Non-woven Web. U.S. Pat. No. 6,202,2001 issued Mar. 20, 2001 to Hill relates to a Folding and Stacking Configuration for Wet Wipes. Lastly, U.S. Pat. No. 6,596,681 issued Jul. 22, 2003 to Mahieu relates to an Antibacterial Cleaning Wipe.

While these devices fulfill their respective, particular objectives and requirements, the aforementioned patents do not describe an herbal remedy system that allows therapeutically treating patients suffering from a wide range of maladies.

In this respect, the herbal remedy system according to the present invention substantially departs from the conventional concepts and designs of the prior art, and in doing so provides an apparatus primarily developed for the purpose of therapeutically treating patients suffering from a wide range of maladies.

Therefore, it can be appreciated that there exists a continuing need for a new and improved herbal remedy system which can be used for therapeutically treating patients suffering from a wide range of maladies. In this regard, the present invention substantially fulfills this need.

SUMMARY OF THE INVENTION

In view of the foregoing disadvantages inherent in the known types of herbal remedies of known compositions now present in the prior art, the present invention provides an improved herbal remedy system. As such, the general purpose of the present invention, which will be described subsequently in greater detail, is to provide a new and improved herbal remedy system and method which has all the advantages of the prior art and none of the disadvantages.

To attain this, the present invention essentially comprises an herbal remedy system to therapeutically treat patients with a wide range of maladies. First provided is a therapeutic mixture having essentially equal parts of eucalyptus globulus oil and pinus sylvestris oil and thymus vulgaris oil.

Next provided is a therapeutic oil-based, rub-on composition in an equivalent ratio of about 12 drops of the initial therapeutic mixture and about 3 tablespoon of a carrier liquid including essentially equal parts of olive oil and alcohol and water.

Next a paper handkerchief is provided. The handkerchief is adapted to receive and retain and dispense the therapeutic oil-based, composition.

An envelope is next provided. The envelope is fabricated of a flexible material impervious to liquid and air. The envelope has the paper handkerchief therein. The paper handkerchief is soaked with the therapeutic oil-based, rub-on composition and folded and positioned within the envelope. When the envelope is opened, the soaked and folded handkerchief is removed and unfolded for use by rubbing and covering and wiping a patient.

Lastly, a therapeutic oil-based consumable composition is provided. The consumable composition is in an equivalent ratio of about 60 drops of the therapeutic mixture and about one drop of lavendula officinalis and a consumable carrier of about 3 tablespoons of honey and about 3 tablespoons of sugar syrup and about 2 deci-liters of water.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved herbal remedy system which has all of the advantages of the prior art herbal remedies of known compositions and none of the disadvantages.

It is another object of the present invention to provide a new and improved herbal remedy system which may be easily and efficiently manufactured and marketed.

It is further object of the present invention to provide a new and improved herbal remedy system which is of durable and reliable constructions.

An even further object of the present invention is to provide a new and improved herbal remedy system which is susceptible of a low cost of manufacture with regard to both materials and labor, and which accordingly is then susceptible of low prices of sale to the consuming public, thereby making such herbal remedy system economically available to the buying public.

Even still another object of the present invention is to provide an herbal remedy system for therapeutically treating patients suffering from a wide range of maladies.

Lastly, it is an object of the present invention to provide a new and improved therapeutic mixture having essentially equal parts of eucalyptus globulus oil and pinus sylvestris oil and thymus vulgaris oil.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a plan view of a herbal remedy system constructed in accordance with the principles of the present invention.

FIG. 2 is a cross sectional view of the system taken along line 2-2 of FIG. 1.

The same reference numerals refer to the same parts throughout the various Figures.

DESCRIPTION OF THE PREFERRED EMBODIMENT

Figure 3:
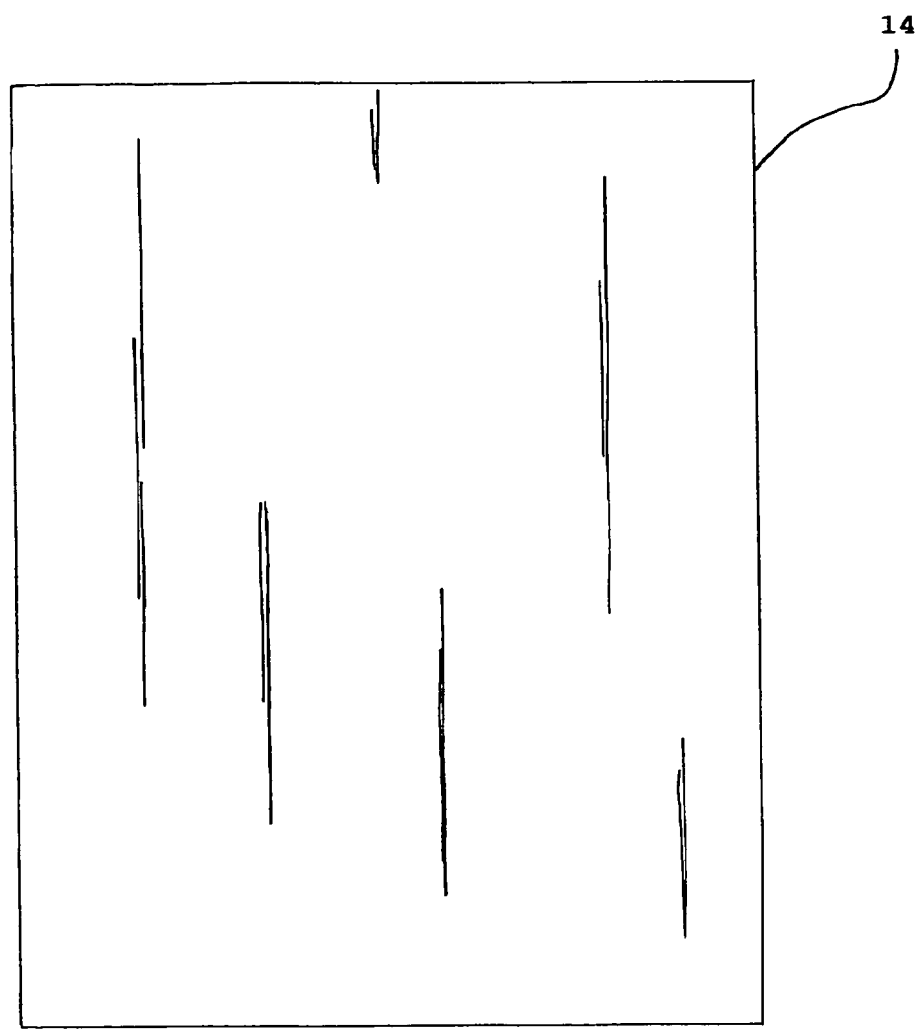
FIG. 3 is a plan view of the oil treated handkerchief of FIG. 1 in an unfolded orientation outside of its envelope.

With reference now to the drawings, and in particular to FIGS. 1 and 2 thereof, the preferred embodiment of the new and improved herbal remedy system embodying the principles and concepts of the present invention and generally designated by the reference numeral 10 will be described.

The present invention, the herbal remedy system 10 is a therapeutic mixture having essentially equal parts of eucalyptus globulus oil and pinus sylvestris oil and thymus vulgaris oil.

The herbal remedy system 10 therapeutically treats patients suffering from a wide range of maladies. First provided is a therapeutic mixture having essentially equal parts of eucalyptus globulus oil and pinus sylvestris oil and thymus vulgaris oil.

Next provided is a therapeutic oil-based, rub-on composition 12 in an equivalent ratio of about 12 drops of the initial therapeutic mixture and about 3 tablespoon of a carrier liquid including essentially equal parts of olive oil and alcohol and water.

Next a paper handkerchief 14 is provided. The handkerchief is adapted to receive and retain and dispense the therapeutic oil-based, rub-on composition.

An envelope 16 is next provided. The envelope is fabricated of a flexible material impervious to liquid and air. The envelope has the paper handkerchief therein. The paper handkerchief is soaked with the therapeutic oil-based, rub-on composition and folded and positioned within the envelope. When the envelope is opened, the soaked and folded handkerchief is removed and unfolded for use by rubbing and covering and wiping a patient.

This kind of rub-on composition can benefit asthma, hay fever, allergies, bronchitis, sinusitis, cough, hoarseness, cold symptoms and lymphatic system by doing a thorough cleansing. This type of fragrant rub-on composition is for external use for rubbing and/or covering and/or wiping. Described below is how to apply and using the composition for many kinds of respiratory problems with great success. Factory made paper handkerchiefs are sprayed with the fragrant oil mixtures then packed and sealed air tight by machines. The patient who wishes to rid himself or herself of some of the mentioned illnesses just opens the package and wipes the face around the nose, forehead and neck. At night, the patient can cover his or her chest with the handkerchief and secure it with a piece of plastic. With this method great results can be achieved.

In addition to the rub-on composition as described above, the present invention also includes therapeutic oil-based consumable composition is provided. The consumable composition is in an equivalent ratio of about 60 drops of the therapeutic mixture and about one drop of lavendula officinalis and a consumable carrier of about 3 tablespoons of honey and about 3 tablespoons of sugar syrup and about 2 deci-liters of water. The rub-on composition and the consumable composition may be used independently of each other or together as a therapeutic regimen.

The consumable composition can be mixed with honey and the olive oil to be used internally, taking it by mouth. Also it could be mixed with combined fragrant oils or an individual fragrant oil. The mixture depends upon the type of illness. A physician or a professional skilled person of herbal medicines must always determine the illness and the type and amount of the suitable herbal medication.

To prove the beneficial effects of herbal remedies as described herein, a few examples of bacterium caused illnesses and the results after applying the remedies include: the meningococcus, meningitis, causing bacterium was destroyed in 15 to 20 minutes; the typhoid fever pathogen was described in 1 hour; the pneumococcus, pneumonia, was destroyed in 2 to 3 hours; the bacterium which cases suppuration was destroyed in 2 to 3 hours; the streptococcus haemolyticus, tonsillitis, erysipelas, scarlet fever, child bed fever pathogen was destroyed in 3 to 12 hours; the diphtheria causing bacteria was destroyed in 20 to 30 minutes.

As to the manner of usage and operation of the present invention, the same should be apparent from the above description. Accordingly, no further discussion relating to the manner of usage and operation will be provided.

With respect to the above description then, it is to be realized that the optimum proportional relationships for the components of the invention, to include variations in amounts, materials, function and manner of operation and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An herbal remedy system for treating patients comprising,
   a therapeutic oil-based, rub-on composition in an equivalent ratio of about 12 drops of a therapeutic mixture and about 3 tablespoon of a carrier liquid including essentially equal parts of olive oil and alcohol and water;
   a paper handkerchief adapted to receive and retain and dispense the therapeutic oil-based, rub-on composition; and
   an envelope fabricated of a flexible material impervious to liquid and air, wherein the envelope contains the paper handkerchief soaked with the therapeutic oil-based, rub-on composition, for use by rubbing and covering and wiping a patient; and a therapeutic oil-based consumable composition in an equivalent ratio of about 60 drops of a therapeutic mixture and about one drop of lavendula officinalis and a consumable carrier of about 3 tablespoons of honey and about 3 tablespoons of sugar syrup and about 2 deci-liters of water;

wherein said therapeutic mixture comprises essentially equal parts of eucalyptus globulus oil and pinus sylvestris oil and thymus vulgaris oil.

* * * * *